(12) United States Patent
Painchaud et al.

(10) Patent No.: US 8,986,266 B2
(45) Date of Patent: Mar. 24, 2015

(54) DEVICE FOR DISPENSING LIQUID IN THE FORM OF DROPS

(75) Inventors: Gaetan Painchaud, Francheville (FR); Guillaume Grevin, L'Isle d'Abeau (FR); Xavier Julia, Villefontaine (FR); Thierry Decock, Paris (FR); Thierry Rimlinger, L'Isle d'Abeau (FR)

(73) Assignee: Nemera la Verpillière S.A.S. (FR)

( * ) Notice: Subject to any disclaimer, the term of this patent is extended or adjusted under 35 U.S.C. 154(b) by 156 days.

(21) Appl. No.: 13/457,613

(22) Filed: Apr. 27, 2012

(65) Prior Publication Data

US 2012/0296291 A1 Nov. 22, 2012

Related U.S. Application Data

(63) Continuation of application No. PCT/FR2010/052258, filed on Oct. 22, 2010.

(30) Foreign Application Priority Data

Oct. 29, 2009 (FR) ...................................... 09 57640

(51) Int. Cl.
| | |
|---|---|
| A61M 35/00 | (2006.01) |
| B05B 11/04 | (2006.01) |
| A61F 9/00 | (2006.01) |
| A61M 15/08 | (2006.01) |
| B05B 1/30 | (2006.01) |
| B05B 11/00 | (2006.01) |
| A61M 11/00 | (2006.01) |

(52) U.S. Cl.
CPC ............. *B05B 11/047* (2013.01); *A61F 9/0008* (2013.01); *A61M 15/08* (2013.01); *B05B 1/30* (2013.01); *B05B 11/0064* (2013.01); *A61M 11/008* (2013.01); *A61M 2210/0612* (2013.01)
USPC .......................................... 604/298; 604/295

(58) Field of Classification Search
USPC .......... 604/289–302; 222/212–215, 476–487, 222/494–497; 137/511–512, 846–856
See application file for complete search history.

(56) References Cited

U.S. PATENT DOCUMENTS

| | | | |
|---|---|---|---|
| 4,334,500 A | 6/1982 | Ziller | |
| 5,373,972 A * | 12/1994 | Bystrom et al. | ............... 222/212 |

(Continued)

FOREIGN PATENT DOCUMENTS

| | | |
|---|---|---|
| EP | 0602019 A2 | 6/1994 |
| EP | 1454839 A2 | 9/2004 |

(Continued)

OTHER PUBLICATIONS

International Search Report; Application No. PCT/FR2010/052258; Issued: Feb. 17, 2011; Mailing Date: Feb. 24, 2011; 2 pages.

*Primary Examiner* — Philip R Wiest
(74) *Attorney, Agent, or Firm* — St. Onge Steward Johnston & Reens LLC

(57) ABSTRACT

A device for dispensing liquid including a liquid reservoir which can be deformed so as to dispense liquid by pressing on the reservoir, a liquid-dispensing end piece fitted on the reservoir, a channel for the passage of liquid, a channel for the passage of air from the outside to the inside of the reservoir, the channel for the passage of air being closed off by a member made of an air-permeable polymeric material, this material being non-porous, the member being called the air-permeable member.

19 Claims, 1 Drawing Sheet

(56) References Cited

U.S. PATENT DOCUMENTS 7,476,212 B2 * 1/2009 Spearman et al. .............. 604/23
2004/0074925 A1 4/2004 Faurie

FOREIGN PATENT DOCUMENTS

| WO | 9201625 A1 | 2/1992 |
| WO | 9322360 A1 | 11/1993 |
| WO | 2006000897 A1 | 1/2006 |

* cited by examiner

DEVICE FOR DISPENSING LIQUID IN THE FORM OF DROPS

CROSS-REFERENCE TO RELATED APPLICATIONS

The present application is a continuation of pending International Patent Application PCT/FR2010/052258 filed on Oct. 22, 2010 which designates the United States and claims priority from French Patent Application 0957640 filed on Oct. 29, 2009, the content of which is incorporated herein by reference.

FIELD OF THE INVENTION

This invention concerns the field of liquid dispensing, especially in the form of drops, in the pharmaceutical field, for example ophthalmic liquid.

BACKGROUND OF THE INVENTION

In particular, the invention concerns the dispensing of preservative-free liquid, in the form of drops, using a deformable reservoir with air intake.

The current trend is to supply products, especially ophthalmic products, that do not contain preservatives. The sterility of the product must thus be guaranteed throughout the use of the bottle containing the liquid to be delivered.

From document WO92/01625, various devices are known that enable the delivery of drops of product contained in a reservoir and which prevent contamination of the liquid remaining in the bottle.

According to one example, such a liquid-dispensing device includes a reservoir and a dispensing end piece fitted on the reservoir, provided with a liquid-dispensing opening. The user applies pressure to the reservoir causing it to become deformed and, under the effect of pressure, a drop forms on the surface of the dispensing opening. Once the drop has been dispensed, the user releases the pressure on the deformable reservoir, which tends to take up its initial shape, generating a depression inside the bottle. To fill this depression and allow the reservoir to return to its initial shape, the end piece of the device comprises an air inlet in the reservoir. To ensure that the incoming air cannot contaminate the liquid remaining in the reservoir, a hydrophobic filter is fitted in the air channel. This filter allows the exterior air to enter the reservoir while avoiding the entry of microorganisms and dust, and preventing liquid from entering or leaving.

One problem with this type of device lies in the fact that it is difficult to guarantee its reliability. It is in fact difficult to test correct operation of the filter after fitting on the end piece, since the filter would have to be tested under water, which implies a risk of contamination or degradation during the test phase. It is therefore difficult to guarantee the integrity of the filters used and of their assembly on the end piece.

The present invention is intended to provide a device for dispensing liquid which reliably guarantees the sterility of the dispensing end piece.

SUMMARY OF THE INVENTION

An object of the invention is therefore a device for dispensing liquid, characterised in that it comprises:
  a liquid reservoir which can be deformed so as to dispense liquid by pressing on the reservoir,
  a liquid-dispensing end piece fitted on the reservoir,
  a channel for the passage of liquid,
  a channel for the passage of air from the outside to the inside of the reservoir, the channel for the passage of air being closed off by a member made from air-permeable polymeric material, this material being non-porous, the member being called the air-permeable member.

It is therefore proposed to perform the function of allowing uncontaminated air into the reservoir, not by filtering the air but by using the gas diffusion properties of some materials. A member made from non-porous polymeric material is therefore used instead of a filter. This type of member offers the advantage of allowing uncontaminated air to flow in a way that is more reliable than with a filter, which is porous by definition. With a non-porous member, in fact, there is no need to test the pore size and it is easier to check that there are no leaks due to poor assembly or a defective member.

A "non-porous" material means a solid material, with no holes, blocking the passage of particles such as bacteria, for example blocking bacterium Brevundimonas Diminuta which has a diameter of about 0.2 micrometers. This non-porous material differs from a filter, which is designed to be porous. The non-porous material proposed for the air-permeable member is in fact composed of a polymer used in its raw form, having undergone for example simple injection or compression, whereas a porous material like that of a filter is composed of a polymer which has also undergone steps to generate pores or interstices, for example stretching of the material or addition of a chemical solvent in the polymer. Since the material is non-porous, it is liquid-tight and blocks the passage of particles such as dust or microorganisms. This material is air-permeable, however, since it allows elements of the size of a molecule to pass through. In other words, the non-porous material proposed above is permeable to gases and allows the air molecules to pass, through a cross-linked network of long tangled molecular chains. In other words, the member made of non-porous material is configured to allow air to pass by diffusion across the air-permeable member. One can see that, since the material is non-porous, air takes several minutes, or even hours, to cross the member, not just a few seconds as is the case for a filter. For a device used to dispense 240 µL of liquid, for example, the depression is almost completely compensated, i.e. the pressures inside and outside the bottle are almost the same after just 12 hours. The time required to return to a pressure more or less equal to the external pressure may seem long, but the inventors of the invention observed that this is not really a problem for application to dispensing of drops.

When the user releases the pressure on the reservoir, after having pressed it to dispense a drop of liquid, the depression between the inside and outside of the bottle is slowly compensated by the flow of external air across the air-permeable member.

It is to be noted that since this member has no pores, there is no risk of clogging due to an accumulation of microorganisms and dust in the pores. In addition, there is no risk of liquid capillary pressure, which would oppose the return to pressure equilibrium between the inside and the outside of the reservoir when the device is upside down and the liquid is in contact with the air-permeable member. These two phenomena are present when a filter is used.

This type of member is very easy to test. All the blocking members can be tested after fitting on the end piece, without contaminating or degrading the member. These types of test are more advantageous than those performed on filters, which are likely to contaminate or degrade them during the tightness test, or for which only statistical tests can be conducted, on samples destroyed during the test, producing relatively limited information.

The members can be tested for example by applying air pressure on one side of the member and measuring the pressure on the other side after a few seconds. Since the process allowing the pressures on each side of the member to return to equilibrium takes several minutes, or even hours, and not just a few seconds, the time scale is not the same as when testing a filter. At the scale of the second, therefore, it will be impossible to detect a pressure loss on a non-defective member, whereas there will be a noticeable pressure drop if the member is defective or badly fitted on the end piece. This test can therefore be used to identify all defective parts. It is to be noted that the air-permeable member can be manufactured easily and cheaply. It therefore differs from the hydrophobic filter, which is very expensive to manufacture, firstly to guarantee fine filtration and secondly to guarantee its integrity.

The dispensing device may also comprise one or more of the following characteristics.

The air-permeable member further comprises at least one channel for the passage of liquid. A member offering a large exchange area with the reservoir can therefore be planned.

The channel for the passage of liquid is a liquid flow limitation channel opening to the channel for the passage of liquid. It is therefore possible to limit the flow of liquid leaving the reservoir and avoid dispensing the liquid in a stream if the user exerts too much pressure on the reservoir. The air-permeable member can therefore be used to act as flow limiter, which makes it easier to assemble the end piece, by reducing the number of parts to be assembled. According to one example, the diameter of the flow limitation channel is relatively small compared with that of the channel for the passage of liquid, or the flow limitation channel has sudden changes of direction, which reduces the pressure.

The end piece and the member each has a central axis, the two axes being colinear. This makes it easier to fit the member on the end piece. It is in fact easy to centre one part with respect to the other. In addition, by placing the air-permeable member in the centre of the device, it can be designed to have a relatively large area, for example covering the entire neck of the device reservoir, thereby offering a larger area for the flow of air, so that the internal and external pressures reach equilibrium as quickly as possible.

The member comprises a so-called air passage wall, equipped with a plurality of reliefs, to increase the air passage area. For example, the wall could be corrugated, have a sinusoidal, castellated or saw-tooth cross-section. This increases the air exchange area between the inside and outside of the reservoir without making the member very much larger. The flow of air that can pass through the member wall by permeability is in fact directly proportional to the exchange area and inversely proportional to the thickness of the member wall. A large exchange area and a thin wall improve the air intake. The member wall geometry can easily be modified by varying the exchange area and thickness parameters to adapt to the rate of air intake required. The reliefs formed on the wall differ from ribs, they are made in parallel on both sides of the member wall, the wall thickness being substantially constant along the reliefs and small enough to allow air to flow, so as to increase the exchange area of the air-permeable member.

The member comprises stiffening ribs. This ribs make the member more rigid. Such ribs correspond to local increases in the thickness of the member wall, to make it more rigid, thereby forming projections on one of the two sides of the wall. These ribs therefore differ from the reliefs described above, whose purpose is to increase the exchange area.

The member has a generally cylindrical or conical shape, with a base comprising a collar for fastening to the end piece. The thickness of this collar is preferably greater than that of the air passage wall, so that it is rigid enough to fasten the member, for example by mechanical tightening. The collar may possibly comprise mechanical fastening means, which cooperate with means on the end piece, for example by snap fastening. Through the use of the collar, the member fits easily on the end piece and requires no complex fastening means. In addition, for a given end piece, it is easy, depending on the required air intake characteristics, to propose a member whose air passage wall can have different configurations, while retaining a standard collar which adapts to the end piece.

The channel for the passage of liquid is defined by an outer annular surface of the air-permeable member. Consequently, there are no holes through the air-permeable member allowing the passage of liquid, which means that the air passage and the liquid passage can be separated.

The polymeric material comprises an elastomer material. Since the member can be deformed, it may possibly be fitted on the end piece by slight deformation. Once in position, the member can return to its initial shape and be fastened by mechanical tightening in the end piece, which simplifies its positioning. In addition, due to the flexibility of the elastomer, it is easier to avoid gaps between the member and the end piece, by adapting the member contact surfaces with the end piece walls.

The polymeric material includes silicone (also called polysiloxane, an inorganic compound consisting of a silicon-oxygen chain). The permeability of silicone to gases further improves the air intake process, shortening the time required. Silicone also offers the advantage of being inert with respect to pharmaceutical liquids.

Liquid dispensing is controlled by a single valve, which can either take a configuration for blocking liquid or a configuration for dispensing liquid. The device therefore differs from a dispensing device equipped with a pump, device in which there is no need to deform the reservoir to dispense liquid.

The device includes a valve and a support comprising a valve bearing surface to block the passage of liquid, the support comprising the channel for the passage of air and the air-permeable member being attached to the support. The device obtained is therefore highly compact.

The time to balance the pressures inside and outside the reservoir after dispensing liquid is greater than 30 minutes, preferably 1 hour. Although the air intake occurs through a member which does not allow the reservoir to return to its initial configuration almost instantaneously, this disadvantage is offset by the fact that the device proposed guarantees that the air coming from the outside is not contaminated. It is to be noted that this time to return to the initial configuration is greater than 30 minutes or even 1 hour, even if the sealing member is used under optimum conditions, being completely clear. In other words, even when the device is not used upside down (in which case water is in contact with the member) and when it contains no impurities, the gas diffusion time is relatively long, unlike filtration by a filter, when this time is almost instantaneous or at least only about few seconds.

Another object of the invention is a set of two devices as described above, including two identical end pieces, equipped with air-permeable members each having a different configuration. For example, the members have different thicknesses or shapes.

BRIEF DESCRIPTION OF THE DRAWINGS

The invention will be better understood from the following description, given solely by way of example and by referring to the drawings wherein.

DETAILED DESCRIPTION OF THE INVENTION

Figure 1:
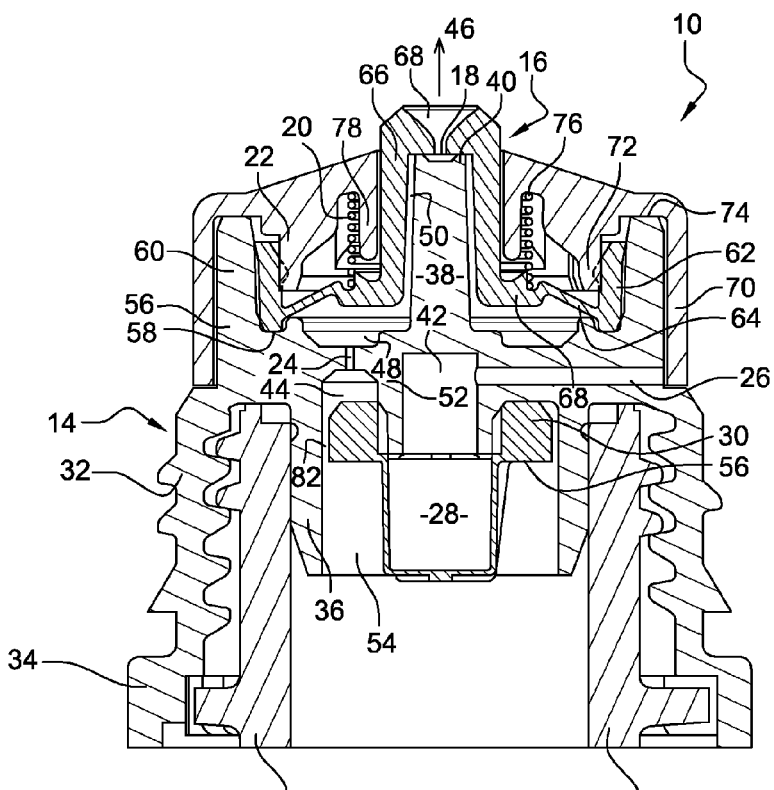
FIG. 1 shows a device according to the invention.

FIG. 1 shows an end piece 10 for dispensing liquid in the form of a drop, for screw mounting onto the neck of a reservoir 12. This reservoir 12 is a storage reservoir for a liquid, for example pharmaceutical liquid such as ophthalmic liquid. The reservoir 12 can be deformed so as to dispense liquid by pressing on the reservoir. More precisely, the liquid is dispensed by pressure, applied by a user, on the body of the reservoir 12, the latter having a certain elasticity to enable it to return to its initial shape after the pressure exerted by the user is released, generating a depression inside the reservoir 12.

In this example, the dispensing end piece 10 comprises a support 14, a dispensing valve 16 equipped with a dispensing opening 18, a spring 20, an outer envelope 22, a channel 24 for the passage of liquid from the reservoir 12 to the dispensing opening 18 and a channel 26 for the passage of air into the reservoir 12, channel 26 being closed off by an air-permeable member 28.

In this example, the support 14 comprises a part 32 for fastening to the reservoir, placed at the proximal end of the support 14. The part 32 comprises an external skirt 34 including a screw thread enabling it to be screwed onto the neck of the reservoir 12. The fastening part 32 also includes a tubular internal skirt 36, enabling it to ensure the seal between the reservoir 12 and the dispensing end piece 10.

Furthermore, the support 14 includes a central sealing part 38, substantially cylindrical in shape and extending in the distal direction, opposite to the internal skirt 36. The part 38 comprises, on its distal end, a bearing surface 40 of the valve 16 to block the flow of liquid in blocking configuration. In this example, the bearing surface 40 has an annular bead shape.

In this example, the support 14 also comprises the channel 26 for the passage of air into the reservoir 12, which opens to a substantially cylindrical cavity 42. This cavity 42 opens, at its proximal end, to the member 28.

In this example, the support 14 also comprises a housing 44 forming a substantially cylindrical cavity, this cavity opening to the reservoir 12 at its proximal end and opening to the channel 24 for the passage of liquid at its distal end, formed in the support 14 and extending in the longitudinal direction of the device, corresponding in this case to the direction of liquid ejection illustrated by the arrow 46. Channel 24 opens to an intermediate cavity 48, itself opening to a second channel 50 for the passage of liquid.

The housing 44 is next to the cavity 42, being separated by an annular wall 52, extending in the direction opposite to the sealing part 38.

The air-permeable member 28 is made of an air-permeable polymeric material, this material being non-porous, blocking the passage of particles such as bacteria of diameter 0.1 micrometers, but allowing molecules, such as air molecules, to pass. Air therefore passes through the air-permeable member 28 by diffusion across the member 28. The polymeric material comprises an elastomer material, silicone in this example. The member 28 has a generally cylindrical or conical shape. Its central axis is colinear with that of the end piece 10, this axis corresponding to the liquid-dispensing direction, therefore to the arrow 46. More precisely, in this example the member 28 comprises a so-called air passage wall, which is relatively thin to improve the exchange of gases, cylindrical or conical in shape, with a top closed off by a disc-shaped surface and a base comprising an annular collar 30 for fastening on the end piece 10, this collar 30 being relatively thick, at least thicker than the general thickness of the air passage wall.

The member 28 is housed in a substantially cylindrical cavity 54 bounded by the internal skirt 36 of the support 14 and is fastened, in this example by mechanical tightening, by cooperation of the collar 30 with the annular wall 52. More precisely, the inner diameter of the collar 30 is slightly less than the outer diameter of the wall 52, such that the collar is held against the wall 52 by elasticity. If necessary, snap fastening means such as an inner annular bead formed on the collar 30 snap fastening into an annular groove formed on the outer surface on the wall 52 may be planned in addition to the mechanical means for fastening the collar 30 on the wall 52. Mechanical attachment means crossing the part 14 to reach the cavity 48 or means for attaching onto the inner wall of the cylinder 36 could also be planned.

In addition, the support 14 comprises a part 56 for fastening the valve 16 on the support 14. This part 56 also acts as part used for fastening the outer envelope 22 on the support 14. It comprises an annular groove 58 bounded on the periphery by an annular wall 60. The annular groove 58 is also bounded, on its inner periphery, by an annular rib created on a wall substantially forming a disc, crossed by the channel 24 and bounding the cavity 48.

The valve 16 can take a configuration for blocking liquid and a configuration for dispensing liquid, by cooperation with the support 14. In this example, it is made from an elastomer material. According to another example, only part of the valve 16 is made from an elastomer material, the other part being made from a more rigid material which can act as seat for the spring 20. The valve 16 comprises a part 62 for fastening to the support 14, forming a substantially tubular skirt. This fastening part 62 is connected to a substantially disc-shaped web 64 and from which a substantially cylindrical central part 66 projects out. The web 64 also comprises a seat 68 for the spring 20. The part 66 forms a substantially cylindrical inner cavity, complementary to the part 38. The part 38 and the cylindrical part 66 are coaxial and jointly bound the channel 50 for the passage of liquid. This channel 50 for the passage of liquid opens to the dispensing opening 18 formed in the distal end of the valve 16, itself opening to a shape 68 for forming drops.

The outer envelope 22 comprises an annular part 70 for fastening on the support 14, as well as another annular part 72, coaxial with the part 70, so as to form a groove 74 housing the annular wall 60. The outer envelope 22 also comprises a seat 76 for the spring 20, extended on its inner periphery by an annular wall 78, crossed by the part 66 and designed to centre the part 66 of the valve 16.

In addition, in this example, the air-permeable member 28 comprises at least one channel 80 for the passage of liquid. Also in this example, the channel 80 for the passage of liquid acts as flow limiter for the liquid, opening to the channel 24 for the passage of liquid. More precisely, the collar 30 of the member 28 comprises on its outer annular surface a plurality of grooves 80, shown in particular on FIGS. 2a to 2d, and delimiting, with the housing 44, channels 82 for reducing the flow of liquid. These channels 82 have a relatively small diameter to reduce the liquid pressure when the user presses on the reservoir. According to an alternative embodiment, the grooves 80 could have changes of direction or a spiral shape. Depending on the number and size of the grooves 80 placed opposite the housing 44, the flow of liquid coming out will be more or less reduced.

For example, the member 28 can take one of the shapes illustrated on FIGS. 2*a* to 2*d*. The reduction shapes 80 are made on the outer periphery of its collar 30, forming a recess in the periphery.

Figures 2A, 2B:
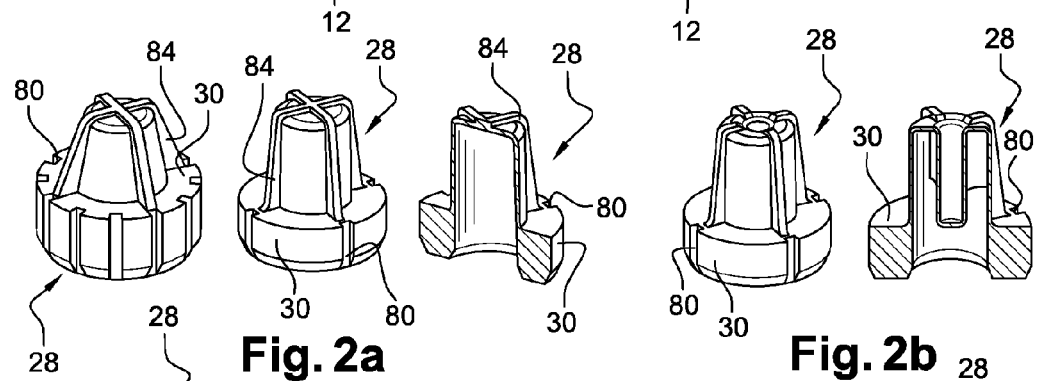
FIGS. 2a to 2d show alternative embodiments of an air-permeable member of the device on FIG. 1.

On the examples of FIG. 2*a*, the member 28 comprises a thin air passage wall, of substantially cylindrical or conical shape. To make it more rigid, the wall also comprises stiffening ribs 84, corresponding to local increases in the thickness of the wall.

Figures 2C, 2D:
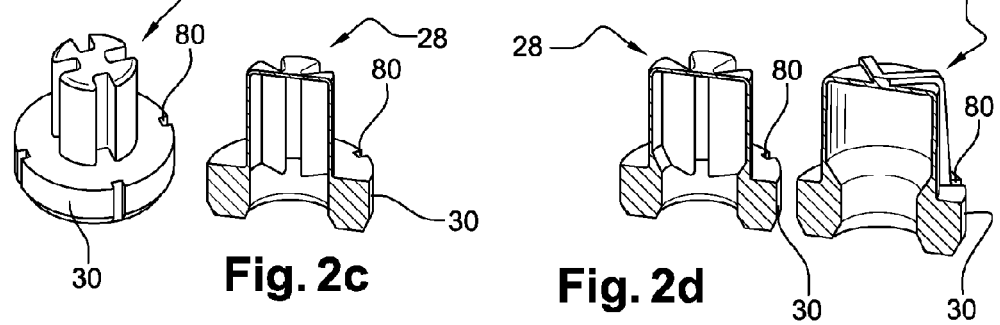

The members 28 of FIGS. 2*b* to 2*d* illustrate other types of member 28 on which the air passage wall comprises, instead of or in addition to the stiffening ribs 84, a plurality of reliefs which increase the air exchange area between the inside and outside of the reservoir 12 without making the member 28 very much larger. These reliefs are formed in the wall so that it remains relatively thin to allow air to pass. In addition, these reliefs can be used to make the member 28 more rigid, possibly avoiding the need for the stiffeners 84, as shown in particular on FIG. 2*c* which illustrates a corrugated air passage wall, having a clover-shaped cross-section.

The operation of the device shown on FIG. 1 will now be described.

At rest, i.e. when no user is pressing the reservoir 12, the valve 16 is in configuration for blocking liquid, i.e. it presses on the surface 40, since it is permanently fastened to the support 14, exerting an elastic force on the valve, and due to the pressure exerted by the spring 20.

A user pressing the reservoir 12 exerts a pressure on the fluid which flows into the only channel allowing it to flow, i.e. the channel 82 for passage of liquid and, in this example, for reducing the flow, since a liquid cannot go through the walls of the member 28. As it passes through this channel 82, in this example, the fluid flow rate decreases, due to the pressure drop. The fluid then flows in the channel 24, then in the cavity 48 and in the channel 50. Under the effect of the pressure, the fluid lifts the valve 16, which then switches into configuration for dispensing liquid, and can therefore flow between the valve 16 and the bearing surface 40, to pass in the channel 18 and in the cavity 68, and therefore take the form of a drop.

Once the drop has been dispensed, the user releases the pressure on the deformable reservoir 12 which tends to take up its initial shape, generating a depression inside the reservoir 12. This depression will be compensated by an intake of exterior air from the channel 26 for the passage of air through the air-permeable member 28. Note that, since the material forming the member 28 is non-porous, air takes several minutes, or even hours, to pass through the member 28, not just a few seconds.

Thus, if we consider a device containing 12 mL, filled with 10 mL of an ophthalmic solution and equipped with an air-permeable member comprising silicone which has an oxygen permeability of $1.4*10^{-13}$ mol*m$^{-1}$*Pa$^{-1}$*s$^{-1}$ (mol per metre per Pascal and per second) and an exchange area of 90 mm$^2$ and a thickness of 0.4 mm, dispensing 6 drops of solution under atmospheric pressure, i.e. 40*6=240 microliters of liquid, creates a depression of about 95 mbar which will be almost completely compensated in 12 hours (more precisely, about 90 mbar will be compensated after 12 hours).

Since the wall of the member 28 is not porous, this time required for air intake into the reservoir 12 is approximately the same, whether or not the device is upside down.

It is to be noted that since the member 28 is a separate part, its shape can be changed to suit the applications, the air intake times required and the flow rate reductions required. It is therefore possible to manufacture sets comprising end pieces with the same valve 16, the same support 14, the same outer envelope 18, but with different members 28.

The invention is not limited to the previously described embodiments.

One can see that it is especially advantageous to use a non-porous material such as that used for the member 28, since it is very easy to check that this member is functional. If a hydrophobic filter had been used instead of the member 28, it would have been difficult to test, after assembly, that the filter does not leak.

What is claimed is:

1. A device for dispensing liquid, comprising:
   a liquid reservoir which can be deformed so as to dispense liquid by pressing on the reservoir;
   a liquid-dispensing end piece fitted on the reservoir;
   a channel for the passage of liquid; and
   a channel for the passage of air from the outside to the inside of the reservoir, the channel for the passage of air being closed off by an air-permeable member made of a polymeric material, this material being non-porous.

2. The device according to claim 1, wherein the air-permeable member is configured to allow air to pass by diffusion across the air-permeable member.

3. The device according to claim 1, wherein the air-permeable member further comprises at least one channel for the passage of liquid.

4. The device according to claim 3, wherein the channel for the passage of liquid is a liquid flow limitation channel opening to the channel for the passage of liquid.

5. The device according to claim 3, wherein the channel for the passage of liquid is bounded by an outer annular surface of the air-permeable member.

6. The device according to claim 1, wherein the end piece and the air-permeable member each has a central axis, the two axes being colinear.

7. The device according to claim 1, wherein the air-permeable member comprises an air passage wall, equipped with a plurality of reliefs.

8. The device according to claim 1, wherein the air-permeable member comprises stiffening ribs.

9. The device according to claim 1, wherein the air-permeable member has a generally cylindrical or conical shape, with a base comprising a collar for fastening to the end piece by mechanical fastening.

10. The device according to claim 1, wherein the polymeric material includes silicone.

11. The device according to claim 1, including a valve and a support comprising a valve bearing surface to block the passage of liquid, the support comprising the channel for the passage of air, the air-permeable member being attached to the support.

12. The device according to claim 1, wherein a time to balance pressures inside and outside the reservoir after dispensing liquid, via the passage of air through the air-permeable member, is greater than 30 minutes.

13. The device according to claim 4, wherein the channel for the passage of liquid is bounded by an outer annular surface of the air-permeable member.

14. The device according to claim 9, wherein the collar comprises mechanical fastening means which cooperate with means on the end piece by snap fastening.

15. A device for dispensing liquid, comprising:
   a liquid reservoir which can be deformed so as to dispense liquid by pressing on the reservoir;
   a liquid-dispensing end piece fitted on the reservoir;
   a channel for the passage of liquid; and
   a channel for the passage of air from the outside to the inside of the reservoir, the channel for the passage of air being closed off by an air-permeable member made of a polymeric material, this material being non-porous;

a plurality of liquid flow limitation channels for passing liquid spaced around a perimeter of the air-permeable member.

16. The device according to claim 15, wherein the air-permeable member is configured to allow air to pass by diffusion across the air-permeable member.

17. The device according to claim 15, wherein the air-permeable member has a generally cylindrical or conical shape, with a base comprising a collar for fastening to the end piece by mechanical fastening.

18. The device according to claim 17, wherein the air-permeable member, including the base and the collar, consists of the polymeric material.

19. The device according to claim 9, wherein the air-permeable member, including the base and the collar, consists of the polymeric material.

\* \* \* \* \*